(12) United States Patent
Pryzdial (10) Patent No.: US 7,671,013 B2
(45) Date of Patent: Mar. 2, 2010

(54) COAGULATION PROTEINS, COAGULATION-ANTICOAGULATION PROTEIN COMPLEXES, DERIVATIVES THEREOF AND THEIR USES

(75) Inventor: Edward L. G. Pryzdial, Vancouver (CA)

(73) Assignee: Canadian Blood Services, Inc. (CA)

( * ) Notice: Subject to any disclaimer, the term of this patent is extended or adjusted under 35 U.S.C. 154(b) by 683 days.

(21) Appl. No.: 11/451,959

(22) Filed: Jun. 13, 2006

(65) Prior Publication Data
US 2007/0025979 A1 Feb. 1, 2007

Related U.S. Application Data

(63) Continuation-in-part of application No. 10/551,565, filed as application No. PCT/CA2004/000493 on Apr. 2, 2004.

(60) Provisional application No. 60/459,647, filed on Apr. 3, 2003.

(51) Int. Cl.
*A61K 38/36* (2006.01)
(52) U.S. Cl. .......................... 514/2; 530/384
(58) Field of Classification Search .................. None
See application file for complete search history.

(56) References Cited

U.S. PATENT DOCUMENTS 7,378,393 B2 * 5/2008 Wun ........................... 514/12

FOREIGN PATENT DOCUMENTS

| EP | 0651054 A1 | 5/1995 |
|---|---|---|
| EP | 0680764 A2 | 11/1995 |
| EP | 0761686 A2 | 3/1997 |
| WO | 91/02532 A2 | 3/1991 |
| WO | 92/04378 A1 | 3/1992 |

OTHER PUBLICATIONS coagulation factor X from *Homo sapiens*, NCBI Reference Sequence: NP_000495.1, printed Mar. 23, 2009.*

Gladstone, D.J., et al., CMAJ, 165(3):311-317 (2001). "Update on intravenous tissue plasminogen activator for acute stroke: from clinical trials to clinical practice."
Llevadot, J. et al., JAMA, 286(4):442-449 (2001). "Bolus fibrinolytic therapy in acute myocardial infarction."
Grundy et al., Biochemistry, 2001, 40:6293-6302. "Binding of Plasminogen and Tissue Plasminogen Activator to Plasmin-Modulated Factor X and Factor Xa."
Pryzdial and Kessler, The Journal of Biological Chemistry, 1996, 271(28): 16621-16626. "Kinetics of Blood Coagulation Factor Xa-alpha Autoproteolytic Conversion to Factor Xa-Beta."
Pryzdial and Kessler, The Journal of Biological Chemistry, 1996, 271(28): 16614-16620. "Autoproteolysis or Plasmin-mediated Cleavage of Factor Xa-alpha Exposes a Plasminogen Binding Site and Inhibits Coagulation."
Pryzdial et al., The Journal of Biological Chemistry, 1999, 274(13): 8500-8505. "Plasmin Converts Factor X from Coagulation Zymogen to Fibrinolysis Cofactor."
Pryzdial et al., The Journal of Biological Chemistry, 1995, 270(30): 17871-17877. "Prothrombinase Components Can Accelerate Tissue Plasminogen Activator-catalyzed Plasminogen Activation."
Zeibdawi and Pryzdial, The Journal of Biological Chemistry, 2001, 276(23), 19929-19936. "Mechanism of Factor Va Inactivation by Plasmin."

* cited by examiner

*Primary Examiner*—Cecilia Tsang
*Assistant Examiner*—Christina Bradley
(74) *Attorney, Agent, or Firm*—Nixon Peabody LLP (57) ABSTRACT

The present invention relates to the use of coagulation proteins and complexes thereof with anticoagulation proteins for the lysis of blood clots or other applications affected by accelerated plasmin production. More specifically, the present invention provides a method for accelerating the dissolution of a blood clot through the administration of at least one coagulation protein, with or without being in complex with a serpin, comprising a basic C-terminal amino acid, wherein the coagulation protein may be a derivative of Factor X or Factor V or a combination thereof. Pharmaceutical compositions for the treatment and prophylaxis of blood clots are also provided, wherein the methods and products of the present invention advantageously accelerate clot dissolution while potentially minimizing the adverse side-effects, such as hemorrhaging, seen with other clot dissolving agents. The present invention also provides a method for detecting a fibrinolytic potential in a subject.

6 Claims, 7 Drawing Sheets

COAGULATION PROTEINS, COAGULATION-ANTICOAGULATION PROTEIN COMPLEXES, DERIVATIVES THEREOF AND THEIR USES

CROSS REFERENCE TO RELATED APPLICATIONS

This is a continuation-in-part of U.S. patent application Ser. No. 10/551,565 filed Oct. 3, 2005, which is a 371 National Phase Entry application of International application PCT/CA2004/000493, filed Apr. 2, 2004, which designated the U.S. and which claims the benefit under 35 U.S.C. § 119(e) of U.S. Provisional application 60/459,647, filed Apr. 3, 2003, the content of which is incorporated herein by reference.

TECHNICAL FIELD

This invention relates to coagulation proteins, complexes of coagulation and anticoagulation proteins, derivatives thereof and their uses.

BACKGROUND OF THE INVENTION

The flow of blood is regulated by opposing biochemical pathways. A key example is the coagulation pathway, which produces a fibrin clot to seal vascular leaks, and the opposing fibrinolysis pathway, which subsequently dissolves the clot to ensure normal blood flow is restored. Thrombosis is the disease that results when balance is lost and clotting occurs where it should not. By understanding the molecules involved in maintaining blood flow, drugs have been developed that quickly dissolve these thrombi and reduce the tissue damage caused by oxygen deprivation, especially in acute myocardial infarction. The "clot busters" that have had the greatest impact and are under most intense development are analogues of the natural protein, tissue plasminogen activator (tPA), which is an important initiator of fibrinolysis. However, tPA is not a perfect drug, because it is an active enzyme. Its activity not only helps dissolve the target clot, but systemic rather than strictly localized effects also deplete blood of essential coagulation proteins. This is dangerous because administration of the current thrombolytic drugs often leads to haemorrhage. To avoid some of the complications associated with tPA, novel strategies to better initiate clot lysis are required.

SUMMARY OF THE INVENTION

According to the invention there is provided a method for accelerating blood clot dissolution in a subject in need thereof, the method comprising administering to said subject at least one coagulation protein containing a basic C-terminal amino acid, notably lysine, in an amount effective to enhance dissolving said blood clot.

The administration of a site-specific accelerator of clot lysis rather than tPA, an intrinsically active enzyme, has the advantage of minimizing systemic consequences. This alleviates the hemorrhagic concerns associated with the available thrombolytic drugs.

In an aspect of the invention the coagulation protein is a derivative of Factor X or Factor V or a combination thereof.

The derivative of Factor X may be Factor Xa or a 33 kDa fragment of Factor Xa comprising a C-terminal lysine residue at a position selected from Lys330, Lys338, Lys351 and combinations thereof. The derivative of Factor X may alternatively be a 13 kDa fragment of Factor Xa comprising a C-terminal lysine residue at a position selected from Lys435, Lys333, Lys327 and combinations thereof. In addition or alternatively, the derivative of Factor X may comprise a non-covalent heterodimer between a 33 kDa fragment of Factor Xa comprising a C-terminal lysine residue at a position selected from Lys330, Lys338, Lys351 and combinations thereof, and a 13 kDa fragment of Factor Xa comprising a C-terminal lysine residue at a position selected from Lys435, Lys333, Lys327 and combinations thereof.

In a further aspect of the invention, the method for accelerating blood clot dissolution in a subject in need thereof may comprise administering to said subject at least one protein complex of a coagulation protein comprising a basic C-terminal amino acid and an anticoagulation protein, or a derivative thereof, in an amount effective to dissolve said blood clot. In a preferred embodiment, the protein complex is a complex of Factor Xa and antithrombin or derivatives thereof.

The protein complex derivatives may be selected from a 33 kDa Factor Xa fragment comprising a C-terminal lysine residue at a position selected from Lys330, Lys338, Lys351 and combinations thereof; a 13 kDa Factor Xa fragment comprising a C-terminal lysine residue at a position selected from Lys435, Lys333, Lys327 and combinations thereof, the 13 kDa Factor Xa fragment being covalently bound to antithrombin; and a noncovalent heterodimer between the 33 kDa Factor Xa fragment and the 13 kDa Factor Xa fragment covalently bound to antithrombin, including combinations thereof.

In a further aspect of the invention the coagulation protein may be administered to a patient concurrently with a fibrinolytic agent and/or an inhibitor of the coagulation pathway.

In a further embodiment of the invention there is also provided a method for detecting a fibrinolytic potential in a subject, the method comprising: obtaining a blood sample from said subject; and measuring a relative concentration of a coagulation protein comprising a basic C-terminal amino acid or a derivative thereof. In an embodiment, the method comprises measuring a relative concentration of Factor X or a derivative thereof comprising a basic C-terminal amino acid, a protein complex of a coagulation protein comprising a basic C-terminal amino acid and an anticoagulation protein, a derivative of the protein complex, or a combination thereof. The Factor X and protein complex derivatives may be as outlined above. Concentration may be measured using a plurality of known protocols as would be understood by one skilled in the art, such as measuring molar concentration, mass concentration, activity, or specific activity.

Accordingly, the present invention provides a method for accelerating blood clot dissolution in a subject in need thereof, the method comprising: administering to said subject at least one coagulation protein comprising a basic C-terminal amino acid in an amount effective to dissolve said blood clot. In a preferred embodiment, the protein is an anionic phospholipid-binding protein. In another preferred embodiment, the subject has a condition selected from: thrombosis, platelet hyperactivity, cardiac ischemia, wound, cardiovascular disease, atherosclerosis, myocardial infarction or a combination thereof. More preferably, the subject is susceptible to said condition and said administration is prophylactic.

In an embodiment, said at least one coagulation protein is a derivative of Factor X, or Factor X complexed with an anticoagulation protein. More preferably, said derivative is selected from Factor Xaα, Factor Xaβ, Factor Xa33/13, Factor Xa in complex with antithrombin (Xa-AT), Factor Xa33/13-AT or a combination thereof. The derivatives may also be as further defined above. In another preferred embodiment, said at least one coagulation protein is a derivative of Factor V. More preferably, said derivative is Factor Va.

In another embodiment of the present invention, said at least one coagulation protein comprises a derivative of Factor X and a derivative of Factor V.

According to methods of the present invention, administration comprises administering to the subject a pharmaceutical composition comprising said derivative of Factor X, or Factor X complexed with an anticoagulation protein, and an acceptable carrier. More preferably, said derivative of Factor X or Factor X complexed with an anticoagulation protein is selected from Factor Xaα, Factor Xaβ, Factor Xa33/13, Xa-AT and Factor Xa33/13-AT or a combination thereof. The derivatives may also be as further defined above.

In another preferred embodiment of the methods of the present invention, administering comprises administering to the subject a pharmaceutical composition comprising said derivative of Factor V and an acceptable carrier. More preferably, said derivative of Factor V is selected from Factor Va.

In accordance with the methods of the present invention, said pharmaceutical composition further comprises a fibrinolytic agent selected from tissue plasminogen activator, urokinase, streptokinase or a combination thereof. In addition, said pharmaceutical composition may further comprise an inhibitor of thrombin. In a preferred embodiment, said inhibitor of thrombin is selected from hirudin, bivalirudin, lepirudin and heparin or a combination thereof.

In a preferred method of the present invention, said pharmaceutical composition is administered intravenously, intramuscularly, subcutaneously, intraperitoneally or intraarterially or a combination thereof.

The present invention also provides a method for detecting a fibrinolytic potential in a subject the method comprising: (a) obtaining a blood sample from said subject; and (b) measuring a relative concentration of a coagulation protein selected from a coagulation protein comprising a basic C-terminal amino acid, a derivative of a coagulation protein comprising a basic C-terminal amino acid or a combination thereof. In a preferred embodiment, said coagulation protein is selected from a derivative of Factor X or Factor V.

The present invention further provides a method for detecting a fibrinolytic potential in a subject the method comprising: (a) obtaining a blood sample from said subject; and (b) measuring a relative concentration of Factor X or a derivative thereof comprising a basic C-terminal amino acid, a protein complex of a coagulation protein comprising a basic C-terminal amino acid and an anticoagulation protein, a derivative of the protein complex, or a combination thereof. The coagulation protein is preferably Factor Xa and said anticoagulation protein is antithrombin.

The derivatives of Factor X and the Factor Xa-antithrombin complex which are particularly useful in the present method of detecting a fibrinolytic potential in a subject are as outlined above.

The present invention additionally provides a pharmaceutical composition comprising a coagulation protein or coagulation protein-anticoagulation protein complex for the treatment or prophylaxis of blood clotting, wherein said coagulation protein comprises a basic C-terminal amino acid. More preferably, said coagulation protein is a derivative of Factor X or Factor V or a combination thereof. The protein complex is preferably a complex between Factor Xa and antithrombin. In a preferred embodiment, said derivative of Factor X is selected from Factor Xaα, Factor Xaβ, Factor Xa33/13, the protein complex derivatives are selected from Xa-AT and Factor Xa33/13-AT or a combination thereof, and the derivative of Factor V is selected from Va. The Factor X and Xa-AT derivatives may also be as further defined above.

A pharmaceutical composition according to the present invention may additionally comprise a pharmaceutically acceptable carrier, and/or one or more fibrinolytic agents, and/or one or more inhibitors of the coagulation pathway.

Additionally provided in accordance with the present invention is a derivative of a coagulation protein or coagulation protein-anticoagulation protein complex effective for the treatment or prophylaxis of blood clotting. The coagulation protein derivative may be a derivative of Factor X selected from: a 33 kDa fragment of Factor Xa comprising a C-terminal lysine residue at a position selected from Lys330, Lys338, Lys351 and combinations thereof; a 13 kDa fragment of Factor Xa comprising a C-terminal lysine residue at a position selected from Lys435, Lys333, Lys327 and combinations thereof; and a noncovalent heterodimer between a 33 kDa fragment of Factor Xa comprising a C-terminal lysine residue at a position selected from Lys330, Lys338, Lys351 and combinations thereof and a 13 kDa fragment of Factor Xa comprising a C-terminal lysine residue at a position selected from Lys435, Lys333, Lys327 and combinations thereof. The protein complex derivatives are derivatives of a complex between Factor Xa and antithrombin, and may be selected from a 33 kDa Factor Xa fragment comprising a C-terminal lysine residue at a position selected from Lys330, Lys338, Lys351 and combinations thereof; a 13 kDa Factor Xa fragment comprising a C-terminal lysine residue at a position selected from Lys435, Lys333, Lys327 and combinations thereof, the 13 kDa Factor Xa fragment being covalently bound to antithrombin; and a noncovalent heterodimer between the 33 kDa Factor Xa fragment and the 13 kDa Factor Xa fragment covalently bound to antithrombin, including combinations thereof.

The present invention further provides a method of producing a coagulation-anticoagulation protein complex or derivative thereof effective for the treatment or prophylaxis of blood clotting. The method comprises activating Factor X with a Factor X activator, either in a single concerted step in the presence of antithrombin, or optionally in a separate step before or after incubation with antithrombin, and purifying resulting Factor Xa-antithrombin complex (Xa-AT) from the reaction mixture by affinity chromatography. Preferably the Factor X activator comprises Russel's viper venom Factor X activator (RVV), the activation step is simultaneous with the incubating with antithrombin, and is conducted in the presence of CaC12 and benzamidine. The activation and incubation with antithrombin may conducted at any time and temperature that would be apparent to one skilled in the art, typically for approximately 10 minutes at approximately room temperature (about 20-30 degrees C.). The affinity chromatography step is advantageously conducted using a heparin-Sepharose column. A variety of chromatography conditions may be used for the affinity separation based on the knowledge of one skilled in the art, but may be conducted in 20 mM Hepes, 150 mM NaCl, pH 7.4, with eluting to be conducted using 1 M NaCl. The purified product can then be cleaved by either plasmin or Factor Xa enzyme to yield derivatives of the Xa-AT complex selected from a 33 kDa Factor Xa fragment comprising a C-terminal lysine residue at a position selected from Lys330, Lys338, Lys351 and combinations thereof; a 13 kDa Factor Xa fragment comprising a C-terminal lysine residue at a position selected from Lys435, Lys333, Lys327 and combinations thereof, the 13 kDa Factor Xa fragment being covalently bound to antithrombin; and a noncovalent heterodimer between the 33 kDa Factor Xa fragment and the 13 kDa Factor Xa fragment covalently bound to antithrombin, including combinations thereof.

BRIEF DESCRIPTION OF THE DRAWINGS

Further features and advantages of the present invention will become apparent from the following detailed description, taken in combination with the appended drawings, in which:

FIG. 5 shows a Coomassie Blue stained electrophoresis gel of purified Xa-AT and the starting Factor X and AT.

FIG. 6 depicts a schematic of an example of the preparation and cleavage of Xa-AT.

FIG. 7A is a plot of plasmin generation as a function of time at two tested cofactor concentrations demonstrating the acceleration of tPA-dependent plasmin generation by Factor Xa or Xa-AT.

DETAILED DESCRIPTION OF THE PREFERRED EMBODIMENT

It has been recognized that the enzyme directly responsible for dissolving fibrin, plasmin (Pn), can change the function of at least two coagulation proteins, Factor Xa (Xa) and Factor Va (Va). By limited proteolysis these are converted into accelerators of tPA [Pryzdial, E. L. G., Lavigne, N., Dupuis, N., Kessler, G. E. (1999) Journal of Biological Chemistry 274: 8500-8505; Pryzdial, E. L. G. and Kessler, G. E. (1996) Journal of Biological Chemistry 271:16614-16620; and Pryzdial, E. L. G., Bajzar, L. and Nesheim, M. E. (1995) Journal of Biological Chemistry, 270:17871-17877]. This function is only acquired when the Pn-treated Factor Xa and Factor Va are bound to negatively charged phospholipids which are normally localized to the vicinity of a clot. However, the clot itself is the accepted physiological tPA accelerator. Enhanced Pn generation and solubilization of a fibrin clot are thus considered distinct biochemical and physiological processes.

In one embodiment of the present invention there is provided coagulation proteins comprising a basic C-terminal amino acid that significantly accelerates solubilization of blood clots. These coagulation proteins may comprise derivatives of Factor X and Factor V.

Figure 1:
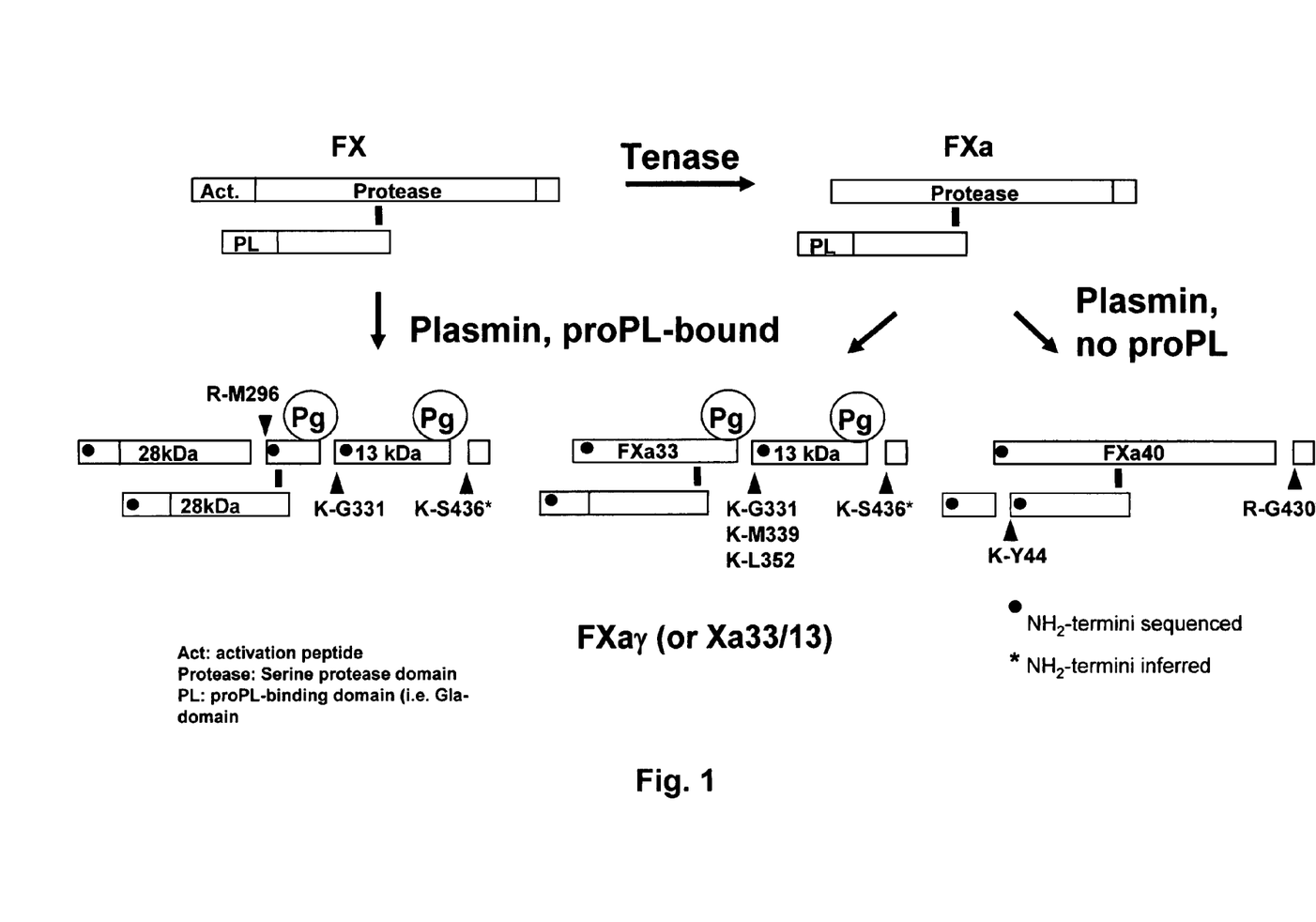
FIG. 1 is a schematic representation of some of the derivatives of Factor X.

Factor Xa: Several compositions of Factor Xa produced by the proteolytic activity of Pn under different conditions were evaluated for enhancement of clot lysis. Factor Xa and Factor X fragments generated by Pn, which we determined earlier [Pryzdial, E. L. G., Lavigne, N., Dupuis, N., Kessler, G. E. (1999) Journal of Biological Chemistry 274:8500-8505 and Pryzdial, E. L. G. and Kessler, G. E. (1996) Journal of Biological Chemistry 271:16614-16620] are summarized in FIG. 1. Binding to procoagulant phospholipid (proPL) alters the cleavage pattern as indicated. When bound to proPL, purified Factor Xa is cleaved twice by Pn to produce fragments of 33, 13 and 3 KDa, which we collectively referred to in earlier reports as Factor Xaγ. An additional minor product of 28 KDa after prolonged Pn-treatment of Factor Xa (28 KDa) has been observed (not shown) and is likely due to cleavage of Factor Xa33 at Met296, as in Factor X. To determine the non-covalent interactions that form between the Factor Xaγ fragments, we have used either proPL coated on microtitre plates or large high density multilamellar vesicles (300 μm) as affinity matrices and by electrophoresis found that Factor Xa33 and 13 KDa remain associated to proPL (not shown)[Grundy, J., Hirama, T., MacKenzie, R. and Pryzdial, E. L. G. (2001) Biochemistry 40:6293-6302]. Since the entire proPL binding site of Factor Xa is contained within Factor Xa33, this observation demonstrates that Factor Xa33 and Xa13 form a non-covalent heterodimer, referred to as Factor Xa33/13. Both Factor Xa33 and Factor Xa13 are predicted by N-terminal sequencing of the successive fragment or by plasminogen binding to contain a C-terminal Lys. For the form of Factor Xa33 capable of accelerating tPA, the predicted C-terminus is either Lys330, Lys338, Lys351 or a mixture of these, which may contain additional C-termini. For either free or Factor Xa13 covalently bound to AT the C-terminus of the tPA accelerating form is predicted to have Lys435, Lys333, Lys327 or a mixture of these. When Factor Xa is subject to proteolysis by plasmin under conditions that do not facilitate binding to proPL, different peptide bonds are cleaved rendering species that likely have C-terminal Arg and do not bind plasminogen effectively, as indicated in the diagram.

Figures 2A, 2B:
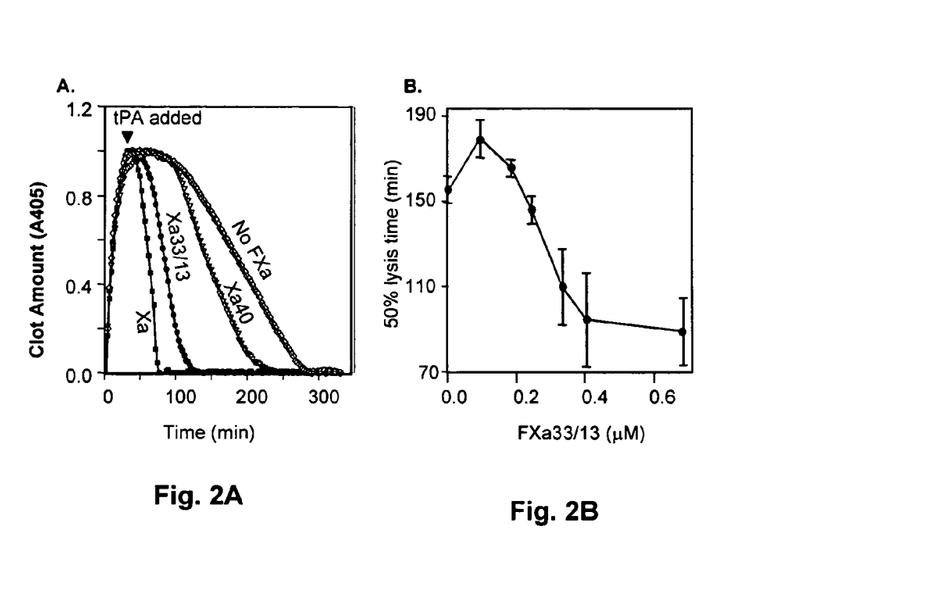
FIG. 2A is plot of clot amount as measured by relative absorbance at 405 nm as a function of time.
FIG. 2B is a plot of the % lysis of clot as a function of Factor Xa33/13 concentration.

Compositions of Factor Xa Accelerate Clot Lysis: Experiments have been conducted by following lysis of a clot that was formed by adding thrombin (3 nM) to a mixture of fibrinogen (3 μM), Pg (0.6 μM), proPL (100 μM), GEMSA (0.1 μM, a carboxypeptidase B inhibitor) and 2 mM Ca2+, in the presence or absence of Factor Xa, Factor Xa33/13 or Factor Xa40 (0.6 μM) (see FIG. 2A). Clot formation and subsequent lysis initiated by addition of tPA (10 nM, arrow) were monitored by turbidity. The rate of clot lysis was found to be greatly enhanced in the presence of Factor Xa33/13 compared to no Factor Xa composition. In the presence of Factor Xa40, the rate of lysis was only slightly enhanced. Although we have found that Factor Xa40 cannot interact with Pg, the slight enhancing effect can be accounted for by the approximately 10% contamination of Factor Xa33/13. When untreated Factor Xa (i.e. a 1:1 mixture of intact Factor Xa (Factor Xaα) and Factor Xa autolytically cleaved to remove a C-terminal 3 KDa fragment (Factor Xaβ) is used in this experiment, an even faster rate of lysis is observed than for Factor Xa33/13. To determine the concentration range over which Factor Xa33/13 is functional in this experiment, a titration has been conducted and the time required to achieve 50% lysis was plotted (see FIG. 2B). With all other parameters constant, this experiment demonstrates a Factor Xa33/13 dose dependence on acceleration of clot lysis. As a comparison, the effect is significantly larger than the initial observation leading to the important discovery of thrombin-activated fibrinolysis inhibitor function. It will be appreciated that other concentrations may also enhance clot lysis depending on the conditions such as pH, temperature and the like as would be obvious to one skilled in the art.

Figure 3:
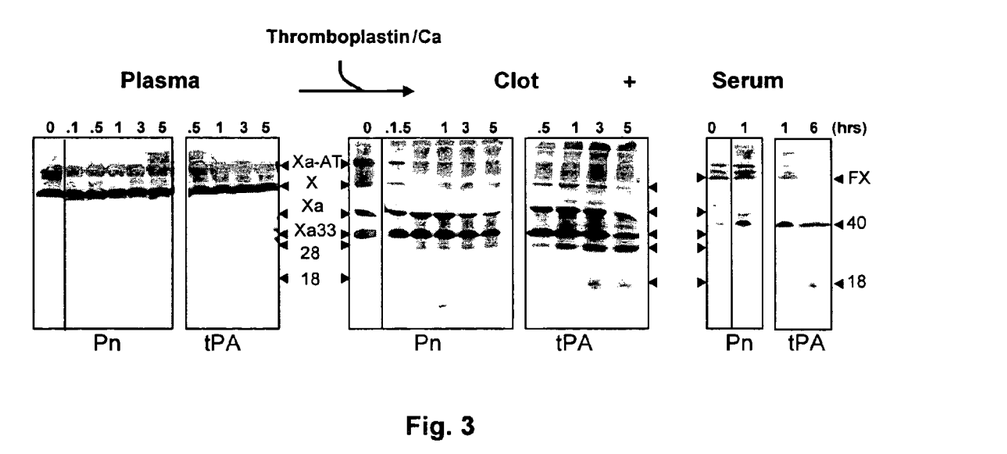
FIG. 3 shows Western blot analyses of electrophoresis gels depicting fragmentation patterns of Factor X in clotted and lysing plasma.

Fragmentation of Factor X and Factor Xa During Clot Lysis in Plasma: To investigate the physiological relevance of Pn-mediated compositions of Factor Xa, experiments were conducted to determine if the fragmentation patterns observed using purified proteins are representative of those formed in the complex plasma milieu. In these experiments, plasma was clotted utilizing thromboplastin as a source of the coagulation initiators, tissue factor and proPL. In this way, Factor Xa is generated during the experiment. Clot lysis was then initiated by addition of Pn (0.1 µM) or tPA (10 nM). Utilizing a Factor X/Factor Xa heavy chain-specific monoclonal antibody (mAb) that detects Factor Xa33 but not Factor Xa13, we conducted Western blot analyses of plasma, clots and serum. The data (FIG. 3) show that treatment of plasma with Pn (2 µM) or tPA (100 nM) for a period of 5 hours at 25° C. has no effect on the distribution of Factor X-derived bands. The latter is approximately half of the predicted therapeutic dose. Multiples of high molecular weight species observed for each experiment represent covalent Factor Xa-serpin complexes of which the probable Factor Xa-antithrombin (Xa-AT) complex is indicated. The highest band in each gel represents IgG which is weakly detected by the mouse secondary antibody used in the detection system. When clot is then formed by adding thromboplastin (as a source of tissue factor) and calcium (Ca2+), it is evident that the majority of Factor X is converted to Factor Xa, which is at least 50% covalently bound by AT or other serpin. Factor Xa33 is visible as a strong band, that in addition to cleavage by Pn, we have observed can be generated much more slowly by autoproteolysis. Since clot formation is allowed to proceed for 30 minutes in these experiments, autoproteolysis could account for part of the production of the Factor Xa33 observed. An important point to note is that Factor Xa33 is recognized by this mAb better than Factor Xa or Factor X and is therefore disproportionately represented. Interestingly, when Pn or tPA is added to the clot, the remaining Factor Xa disappears over time with a concomitant increase in a 28 KDa fragment. Factor Xa33 appears unchanged over the duration of the experiment, but this observation could be only due to the extent of recognition by this mAb. We have previously reported the appearance of this 28 KDa fragment in purified Pn digestions of Factor Xa [Pryzdial, E. L. G. and Kessler, G. E. (1996) Journal of Biological Chemistry 271:16614-16620] as a very minor product. Its identity has been deduced based on antigenicity, size and known cleavages in Factor X, as Factor Xa33, with an extra cleavage at Arg296. Since this would excise the activation fragment in addition to part of the heavy-chain, the 28 KDa species could be derived from either Factor Xa or Factor X. An additional low molecular weight 18 KDa species was observed, which would be expected to occur in molecules that are not bound to proPL by cleavage at Lys43 in the light-chain. An interesting observation is that the 28 and 18 KDa fragments are produced faster when clot is lysed with tPA than with Pn. These data show that the Factor X/Factor Xa cleavage products observed for purified Factor X/Factor Xa proteins also occur in plasma, and therefore support physiological relevance. To determine which Factor X/Factor Xa species are released into serum as the clot is lysed, at various times the dissolving clot was spun and the supernatant was run on gels. In the resulting serum, we observed only Factor Xa-serpin complexes, Factor X, a 40 KDa and the 18 KDa fragment independent of platelets. The 40 KDa species presumably represents a fragment we have also characterized that is formed by cleavage at Lys43 when Factor Xa is not bound to proPL. These observations suggest that nearly all of Factor Xa generated during clot formation in plasma is recruited to the clot. Cumulatively these data support the conclusion that Pn-mediated compositions of Factor Xa and Factor X are generated under physiological conditions. Natural occurrence implies immune tolerance to these peptide bond-modified derivatives of Factor X and Factor Xa, which adds further support for their therapeutic potential.

Use of Coagulation-Anticoagulation Protein Complexes to Accelerate Clot Lysis.

Figure 4:
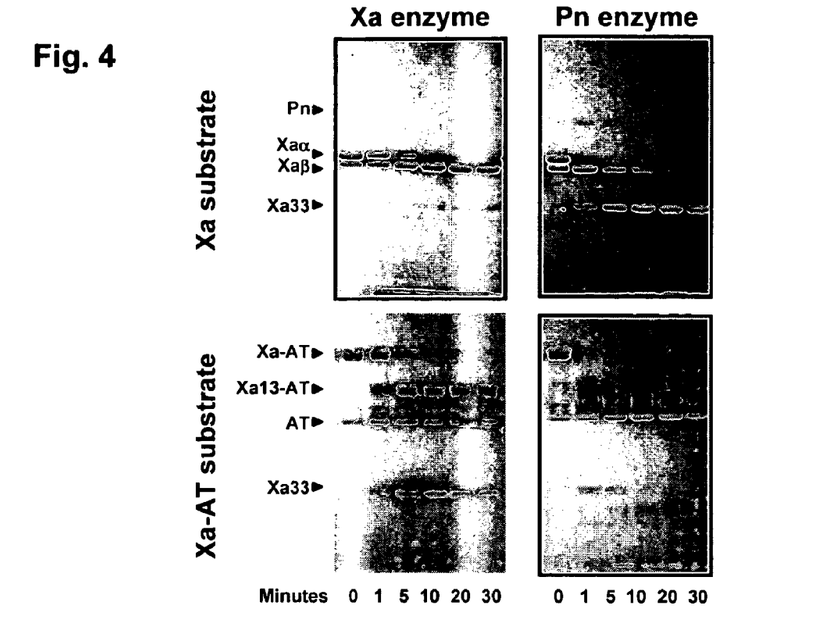
FIG. 4 illustrates Coomassie blue stained electrophoresis gels comparing cleavage of Factor Xa or Xa-AT by Factor Xa or plasmin and demonstrating the generation of a 33 kDa derivative of Factor Xa.

As illustrated herein above, Factor Xa33 and by inference Factor Xa13 are generated in plasma by proteolysis. Since Factor Xa-AT is a potential source for production of Factor Xa33, we investigated the possibility that serpin complexes of coagulation protein Factor Xa may accelerate tPA-dependent plasmin generation. Accordingly, we have found that Xa-AT—a complex of Factor Xa and antithrombin—is cleaved much more rapidly than Factor Xa. The derivative of Xa-AT is commensurate with Factor Xa33 and a covalent complex of Xa13-AT and may therefore be a more effective therapeutic because it is produced at least 10-fold faster than the analogous species derived from Factor Xa (FIG. 4). Furthermore, Xa33/13 derived from Xa-AT and not directly generated from Factor Xa may be the physiological source of fibrinolytic derivatives of Factor Xa. Like Factor Xa33/13, the advantage over existing clot-dissolving therapeutics is that Xa33/13-AT is not an enzyme, but is a cofactor that enhances the existing enzyme, tPA. Therefore using Xa33/13-AT or derivatives as clot-lysing therapeutic may overcome the complication of bleeding observed due to administering current enzyme-based thrombolytic agents, like tPA. As demonstrated by N-terminal amino acid sequencing (not shown) Factor Xa13 remains covalently associated with AT to form a Xa13-AT adduct. Factor Xa33 and Xa13-AT elute from a gel filtration column at the same location as Xa-AT demonstrating that Factor Xa33 and Xa13-AT remain non-covalently associated as Factor Xa33/13-AT under non-denaturing conditions. The ratio of Xa-AT to Factor Xa33 or Xa13-AT may consequently be an indicator of how well clots may lyse in an individual patient and provide a new marker for predicting vascular disease.

It is thus demonstrated herein that a coagulation-anticoagulation protein complex can accelerate the production of plasmin, by tissue plasminogen activator (tPA), and accelerate clot lysis. Accordingly, the potential for coagulation-anticoagulation protein complexes in identifying and treating disorders and conditions of thrombosis and the like is identified for the first time.

As mentioned above, FIG. 4 illustrates that the conversion of Factor Xa to the 33 kDa fibrinolytic species is accelerated when complexed with AT. Shown are Coomassie blue stained gels demonstrating that either plasmin (Pn) or Factor Xa as enzymes (0.1 uM) generate the tissue plasminogen activator cofactor, Factor Xa33, faster when the substrate is Xa-AT compared to Factor Xa alone (5.0 uM). Within one minute all of the Xa-AT is cleaved by plasmin and then further cleaved.

Figure 5:
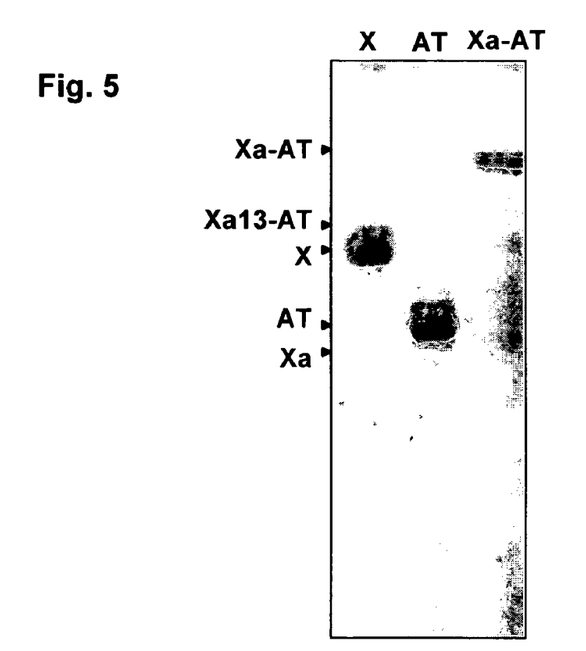
Figure 6:
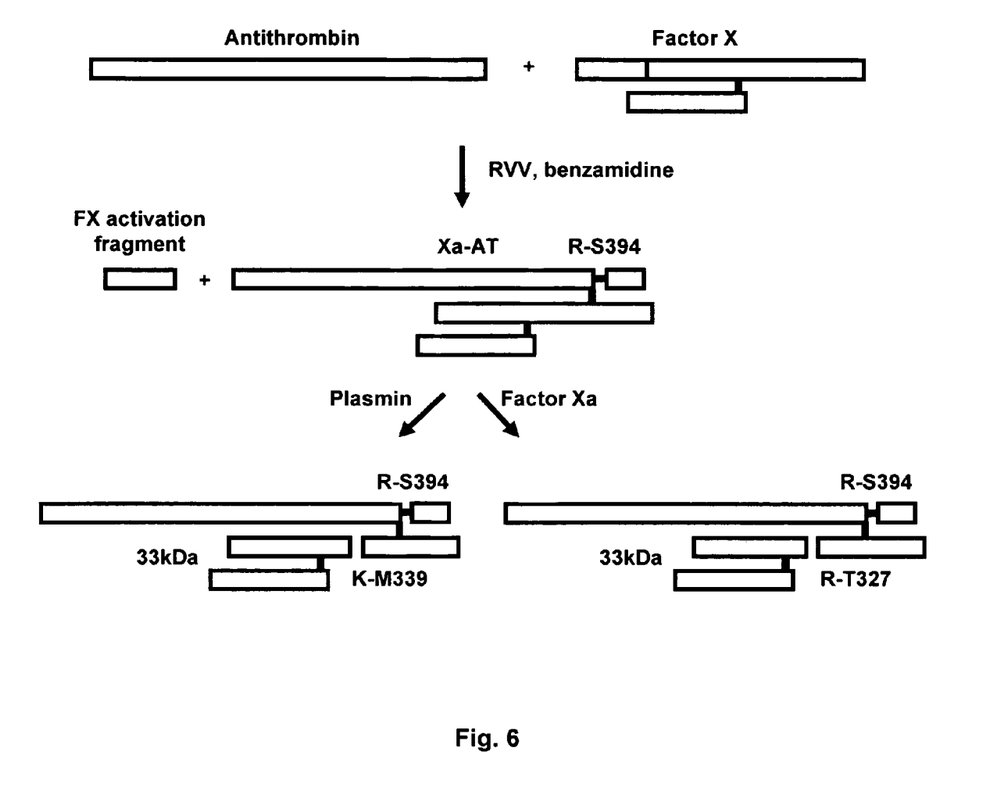

To evaluate function, Xa-AT was prepared from a mixture of Factor X and AT and purified (FIG. 5). In brief, to reduce rapid proteolysis by Factor Xa, Factor X was activated de novo with Russel's viper venom Factor X activator (RVV) in the presence of AT, CaCl2 and benzamidine for approximately 10 minutes at room temperature. The Xa-AT was purified from the reaction mixture by affinity chromatography, i.e. by loading onto a heparin-Sepharose column equilibrated with 20 mM Hepes, 150 mM NaCl, pH 7.4, and eluting with a linear gradient of 1M NaCl. The final product used for functional assays had no measurable RVV or Factor Xa activity. Shown in FIG. 5 is a Coomassie blue stained gel of starting Factor X and AT and the purified Xa-AT product. A method of preparing purified Xa-AT complex is provided in greater detail in Example 1. A general schematic of the preparation and cleavage of Xa-AT into the Factor Xa33 and Xa13/AT derivatives is provided in FIG. 6.

Figure 7A:
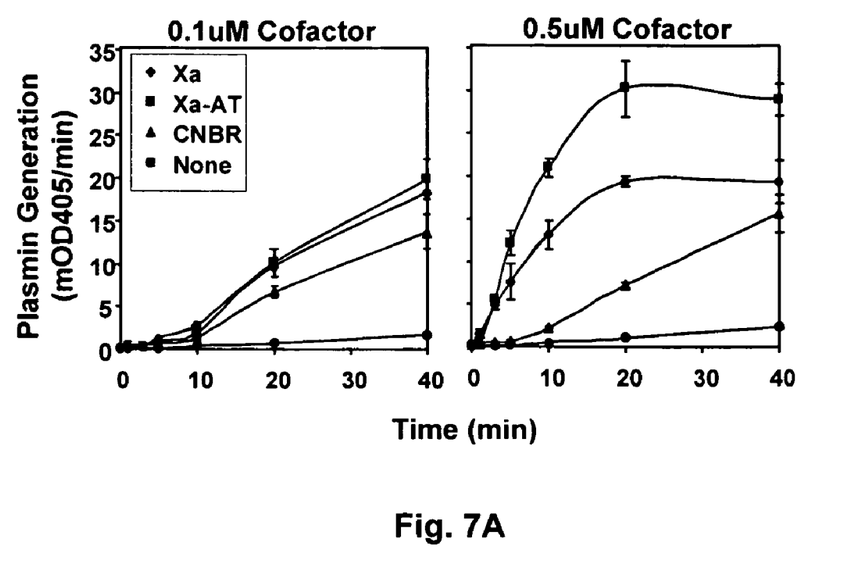
Figure 7B:
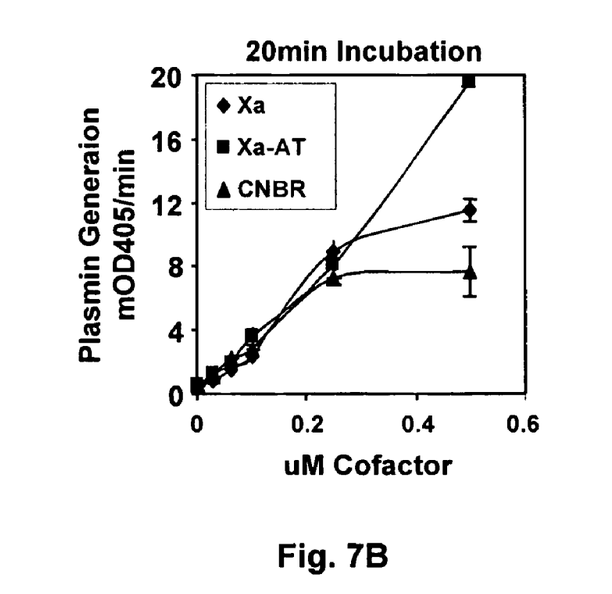
FIG. 7B is a plot of plasmin generation as a function of cofactor concentration demonstrating dose-dependent acceleration of tPA-dependent plasmin generation by Xa-AT and Factor Xa.

As exemplified in FIG. 7a the Xa-AT complex accelerates the production of plasmin by tPA in a manner comparable to Factor Xa alone. Shown are the results of a chromogenic assay to measure plasmin generation from plasminogen (0.5 uM) by tPA (10 nM) that demonstrates acceleration of tPA by either Xa-AT or Factor Xa at the concentrations tested (0.1 uM and 0.5 uM). At the highest concentration tested (0.5 uM), Xa-AT was significantly better at accelerating tPA when compared to Factor Xa and CNBr, a known cofactor used for reference purposes. As illustrated in FIG. 7b, at 0.5 uM cofactor, plasmin generation was enabled for 20 minutes. These data further demonstrate that at the highest concentration used, Xa-AT is better at enhancing tPA function than Factor Xa (n=3).

Figure 8:
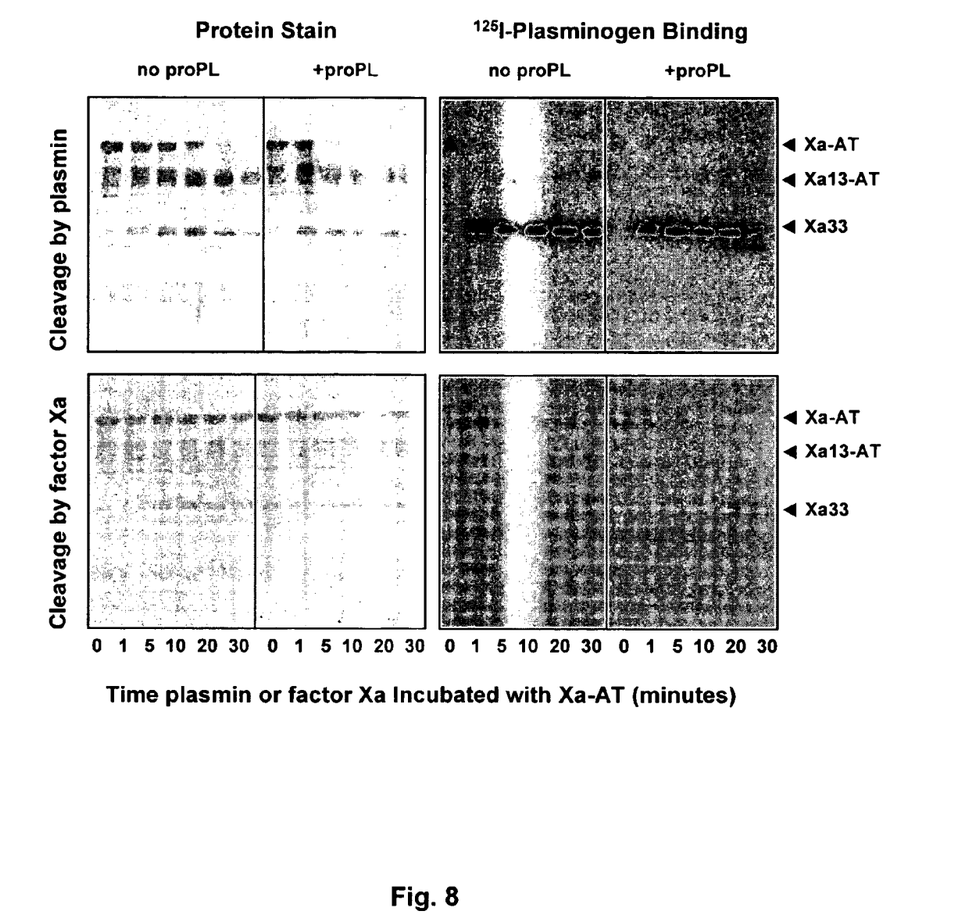
FIG. 8 shows protein stains and ligand blots of the binding of plasminogen to Factor Xa or Xa-AT derivatives produced by Factor Xa- or plasmin-mediated cleavage.

FIG. 8 illustrates a protein stain and a ligand blot (using 125I-labeled plasminogen as a probe), demonstrating that cleavage of Xa-AT by plasmin to form Factor Xa33/13-AT exposes a binding site for plasminogen, particularly on Factor Xa33. Combined with the ability to accelerate plasmin production by tPA, this property supports the conclusion that Factor Xa33/13-AT will be similar to Factor Xa33/13 in aiding clot dissolution or other biological functions dependent on plasmin production, such as tissue remodeling.

Figure 9:
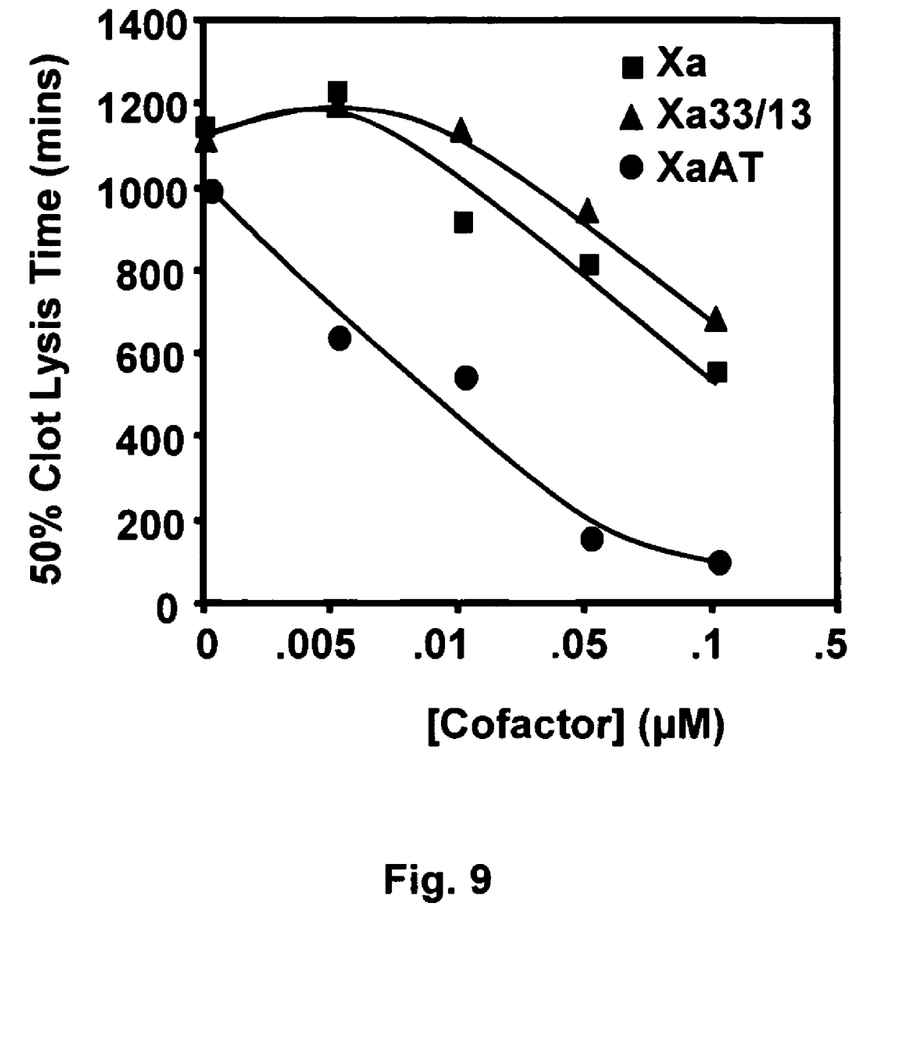
FIG. 9 is a plot of time to achieve 50% clot lysis as a function of cofactor concentration demonstrating acceleration of clot lysis by Xa-AT, Factor Xa33/13 and Factor Xa.

FIG. 9 shows the results of a clot lysis assay which depicts the acceleration of clot lysis by Factor Xa, Factor Xa33/13 and Xa-AT. Briefly, in the presence or absence of Factor Xa, Factor Xa33/13 or Xa-AT, and constant plasminogen concentration (0.6 uM), fibrinogen (3 uM) was induced to clot with 3 nM thrombin. When clot formation was complete, after incubation for 20 minutes, tPA (1.0 pM) was added and clot lysis was followed by turbidity at 405 nm. The time to reach 50% clot lysis was plotted (n=3, SD<10%). As can be seen, Factor Xa and Factor Xa33/13 show a comparable dose-dependent effect in accelerating clot lysis. The Xa-AT complex shows an even greater dose-dependent effect. These data support the use of Factor Xa, Xa-AT and derivatives thereof to enhance clot lysis.

Thus in one embodiment of the invention there is provided a method for treating patients with conditions necessitating an accelerated dissolution of blood clots. The method involves the administration of a coagulation protein or a coagulation-anticoagulation protein complex having a basic C-terminal amino acid capable of accelerating the dissolution of blood clots in the presence of intrinsic or therapeutic tissue plasminogen activator.

Derivatives of the coagulation protein may also be used in the methods and pharmaceutical compositions described herein, either alone or in varying combinations. Derivatives of the coagulation protein Factor X include a 33 kDa fragment of Factor Xa comprising a C-terminal lysine residue at a position selected from Lys330, Lys338, Lys351 and combinations thereof. The Factor X derivatives further include a 13 kDa fragment of Factor Xa comprising a C-terminal lysine residue at a position selected from Lys435, Lys333, Lys327 and combinations thereof. In addition, the Factor X derivatives include a noncovalent heterodimer formed between the aforementioned 33 kDa and 13 kDa fragments of Factor Xa. Furthermore, chemically stabilized or mutated forms of Factor Xa, Factor Xa33/13, Xa-AT or Factor Xa33/13-AT may be prepared to prevent inactivation or prolongation of said fibrinolytic function.

In addition, derivatives of the coagulation-anticoagulation protein complex may be used in the methods and pharmaceutical compositions described herein, either alone or in combination. The preferred coagulation protein for such complexes is Factor X, more preferably Factor Xa, and the anticoagulation protein is preferably antithrombin. The protein complex derivatives include a 33 kDa fragment of the complexed Factor Xa comprising a C-terminal lysine residue at a position selected from Lys330, Lys338, Lys351 and combinations thereof. Also included as a derivative is an antithrombin-bound 13 kDa fragment of the complexed Factor Xa comprising a C-terminal lysine residue at a position selected from Lys435, Lys333, Lys327 and combinations thereof. Such derivatives further include a noncovalent heterodimer between the aforesaid 33 kDa fragment of the complexed Factor Xa and the aforesaid antithrombin-bound 13 kDa fragment of the complexed Factor Xa, and combinations thereof.

Conditions that can be treated in accordance with this method are conditions in which a faster rate of clot dissolution is desirable, conditions in which clot dissolution is abnormally low or conditions that enhanced plasmin generation is desirable. Such conditions may comprise but are not limited to: thrombosis, platelet hyperactivity, cardiac ischemia, wound, cardiovascular disease, atherosclerosis, myocardial infarction or tissue remodeling. It will be appreciated that administration of the coagulation protein or coagulation-anticoagulation protein complex may be prophylactic to patients susceptible to the above mentioned conditions.

Preferred routes of administration are intravenous, intramuscular, subcutaneous, intraperitoneous, and intraarterial. It will be appreciated that other methods of administration may be used such as, for example, local administration at the site of a clot using a catheter.

The coagulation protein or coagulation-anticoagulation protein complex comprising a basic C-terminal amino acid is preferably administered as part of a pharmaceutical composition which may also comprise a pharmaceutically acceptable carrier as would be obvious to one skilled in the art.

It will be appreciated that the coagulation protein or coagulation-anticoagulation protein complex of the present invention may be administered concurrently with one or more fibrinolytic agents such as but not limited to tissue plasminogen activator, urokinase, streptokinase and the like.

It will also be appreciated that the coagulation protein or coagulation-anticoagulation protein complex of the present invention may be administered concurrently with one or more inhibitor of the coagulation pathway. For example, inhibitors of thrombin, such as but not limited to heparin, bivalirudin, liperudin and the like.

In a further aspect of the invention, detection of derivatives of Factor X/Xa, V/Va or the coagulation-anticoagulation protein complex Xa-AT in patient plasma may serve as a clinical marker for fibrinolytic potential. Detection of the fibrinolytic activity can be achieved by obtaining a blood sample from a patient and measuring the relative concentration or activity of a coagulation protein or coagulation-anticoagulation protein complex comprising a basic C-terminal amino acid. It will be appreciated that the coagulation protein or coagulation-anticoagulation protein complex may undergo in vivo modification and that accordingly the method also comprises measuring a concentration of derivatives of the coagulation protein or coagulation-anticoagulation protein complex comprising a basic C-terminal amino acid.

It will be appreciated that the application of Factor Xa fragments herein outlined above may be derived from proteolysis of Xa-AT to render Factor Xa33/13-AT.

EXAMPLE 1

Preparation of Xa-AT:

Chemicals and Reagents. Human plasma-derived Factor X and antithrombin III (AT), and purified Russel's viper venom Factor X activator were purchased from Haematologic Technologies (Essex Junction, Vt., USA). Benzamidine hydrochloride and 4-2-hydroxyethyl-1-piperazineethane-sulfonic acid (HEPES) were purchased from Sigma-Aldrich (Oakville, ON, Canada). Calcium chloride was purchased from EMD Chemicals, Inc. (Gibbstown, N.J., USA). Tetrasodium ethylenediamine tetraacetate (EDTA) was from Fisher Scientific (Nepean, ON, Canada). Heparin Sepharose was obtained from Pfizer (Kirkland, QC, Canada).

Generation of Xa-AT complex. The Xa-AT complex was generated under conditions that would prevent proteolysis by Factor Xa. Factor X (20 µM) and an excess of AT (60 µM) were combined in the presence of 10 mM benzamidine and 2 mM CaC12 in HBS (20 mM HEPES, 150 mM NaCl, pH 7.4). RVV (125 nM) was added and the reaction was incubated at 25oC for 12 minutes. At this time, EDTA (5 mM) was added to stop further generation of Factor Xa during the purification.

Purification of Xa-AT complex. The reaction mixture was loaded onto a 5 mL heparin-Sepharose column by gravity. Subsequent management of the column was done by an ÄKTA Purifier system (Amersham, Piscataway, N.J.). Three column volumes of HBS 10 mM benzamidine, 5 mM EDTA was used to wash the column. All RVV activity was found in the wash. Elution of Xa-AT was accomplished by a linear gradient of wash buffer to which 1M NaCl had been added. SDS-PAGE analysis was used to identify column fractions that contained the Xa-AT, typically eluting at approximately 0.5M NaCl. These fractions were pooled and buffer exchanged into HBS using a Microcon YM10 centrifugal concentrator (Millipore, Cambridge, ON, Canada). The concentration of the final product was quantified by BCA assays (Pierce Biotechnology, Inc., Rockford, Ill.) and confirmed by SDS-PAGE.

INDUSTRIAL APPLICABILITY

The present invention advantageously provides a novel strategy to better initiate clot lysis, while avoiding the complications often associated with current thrombolytic drugs. The products and methods of the present invention provide industrially applicable means for the acceleration of blood clot dissolution, and a method for detecting a fibrinolytic potential in a subject. The invention also provides for enhanced plasmin generation in other applications where plasmin generation is desirable, such as tissue remodeling.

The embodiment(s) of the invention described above is(are) intended to be exemplary only. The scope of the invention is therefore intended to be limited solely by the scope of the appended claims.

I claim:

1. A pharmaceutical composition comprising (i)
   (i) a non-covalent heterodimer of
      (a) a 33 kDa fragment of Factor Xa comprising a C-terminal Lysine residue selected from lys330, Lys338 and Lys351; and
      (b) a 13 kDa fragment of factor Xa comprising a C-terminal Lysine residue selected from Lys435, Lys333 and Lys 327, or a 13 kDa fragment of Factor Xa comprising a C-terminal lysine residue selected from Lys435, Lys333, and Lys327 covalently bound to antithrombin; and
   (ii) an anticoagulation protein.

2. A pharmaceutical composition according to claim 1, further comprising a pharmaceutically acceptable carrier, and/or one or more fibrinolytic agents, and/or one or more inhibitors of the coagulation pathway.

3. A pharmaceutical composition according to claim 1, wherein said anticoagulation protein is antithrombin.

4. A pharmaceutical composition according to claim 1, wherein the anticoagulation protein is a member of a serpin family.

5. A pharmaceutical composition according to claim 1, wherein the pharmaceutical composition is produced by activating Factor Xa with a Factor Xa activator and cleaving the Factor Xa in the presence of antithrombin.

6. A pharmaceutical composition according to claim 5, wherein the activated and cleaved Factor Xa is further purified by affinity chromatography.

* * * * *